(12) United States Patent
Amplatz et al.

(10) Patent No.: US 6,932,837 B2
(45) Date of Patent: Aug. 23, 2005

(54) REPOSITIONABLE AND RECAPTURABLE VASCULAR STENT/GRAFT

(75) Inventors: Kurt Amplatz, St. Paul, MN (US); Michael Afremov, St. Louis Park, MN (US)

(73) Assignee: AGA Medical Corporation, Golden Valley, MN (US)

( * ) Notice: Subject to any disclaimer, the term of this patent is extended or adjusted under 35 U.S.C. 154(b) by 114 days.

(21) Appl. No.: 10/228,230

(22) Filed: Aug. 27, 2002

(65) Prior Publication Data

US 2003/0023299 A1 Jan. 30, 2003

Related U.S. Application Data

(62) Division of application No. 09/535,600, filed on Mar. 27, 2000, now Pat. No. 6,468,301.

(51) Int. Cl.[7] .................................................. A61F 2/06
(52) U.S. Cl. .................... 623/1.15; 623/1.15; 623/1.35; 623/1.53
(58) Field of Search .................. 623/1.1–1.13, 623/1.24–1.26, 1.31, 1.35, 1.37, 1.5–1.53, 1.15; 606/194, 200

(56) References Cited

U.S. PATENT DOCUMENTS

| | | | | |
|---|---|---|---|---|
| 4,202,349 A | | 5/1980 | Jones | 128/689 |
| 4,441,215 A | * | 4/1984 | Kaster | 623/1.53 |
| 5,474,563 A | | 12/1995 | Myler et al. | 606/108 |
| 5,556,414 A | | 9/1996 | Turi | 606/198 |
| 5,562,725 A | | 10/1996 | Schmitt et al. | 623/1 |
| 5,601,595 A | | 2/1997 | Smith | 606/200 |
| 5,669,924 A | | 9/1997 | Shaknovich | 606/108 |
| 5,697,970 A | | 12/1997 | Schmitt et al. | 623/1 |
| 5,709,713 A | * | 1/1998 | Evans et al. | 623/1.53 |
| 5,713,948 A | | 2/1998 | Uflacker | 623/1 |
| 5,720,735 A | | 2/1998 | Dorros | 604/284 |
| 5,749,825 A | | 5/1998 | Fischell et al. | 600/3 |
| 5,776,186 A | | 7/1998 | Uflacker | 623/1 |
| 5,787,900 A | | 8/1998 | Butler et al. | 128/898 |
| 5,800,516 A | | 9/1998 | Fine et al. | 623/1 |
| 5,800,520 A | * | 9/1998 | Fogarty et al. | 623/1.37 |
| 5,824,042 A | | 10/1998 | Lombardi et al. | 623/1 |
| 5,824,055 A | | 10/1998 | Spiridigliozzi et al. | 623/1 |
| 5,855,600 A | | 1/1999 | Alt | 623/1 |
| 5,855,613 A | | 1/1999 | Antanavich et al. | 623/11 |
| 5,868,754 A | | 2/1999 | Levine et al. | 606/108 |
| 5,876,449 A | | 3/1999 | Starck et al. | 623/12 |
| 5,882,335 A | | 3/1999 | Leone et al. | 604/96 |
| 5,891,108 A | | 4/1999 | Leone et al. | 604/264 |
| 5,928,248 A | | 7/1999 | Acker | 606/108 |
| 5,941,896 A | | 8/1999 | Kerr | 606/200 |
| 5,951,569 A | | 9/1999 | Tuckey et al. | 606/108 |
| 6,019,786 A | * | 2/2000 | Thompson | 623/1.13 |
| 6,068,654 A | | 5/2000 | Berg et al. | 623/1 |
| 6,074,416 A | | 6/2000 | Berg et al. | 623/1 |
| 6,149,682 A | | 11/2000 | Frid | 623/1.35 |
| 6,152,945 A | | 11/2000 | Bachinski et al. | 606/198 |
| 6,152,956 A | | 11/2000 | Pierce | 623/1.13 |
| 6,176,873 B1 | * | 1/2001 | Ouchi | 623/1.22 |
| 6,325,826 B1 | * | 12/2001 | Vardi et al. | 623/1.35 |

* cited by examiner

*Primary Examiner*—Tan-Uyen T. Ho
(74) *Attorney, Agent, or Firm*—Thomas J. Nikolai; Nikolai & Mersereau, P.A.

(57) ABSTRACT

A collapsible medical device and associated method for grafting a lumen of selected organs and vessels, wherein the medical device is shaped from a shape memory fabric. The device is preferably made from a continuous tubular fabric and each end terminates with an open end for passage there through. Each end further includes a securing member attached to an outer perimeter of the end, wherein a substantial plane formed by the perimeter intersects the longitudinal axis of the tubular fabric at either an acute or obtuse angle. The fabric may be heat treated within a mold in order to substantially set a desired shape of the device. The securing member may also attach to the end of a guide wire or delivery catheter, thereby allowing deployment and later retrieval after deployment of the device.

10 Claims, 9 Drawing Sheets

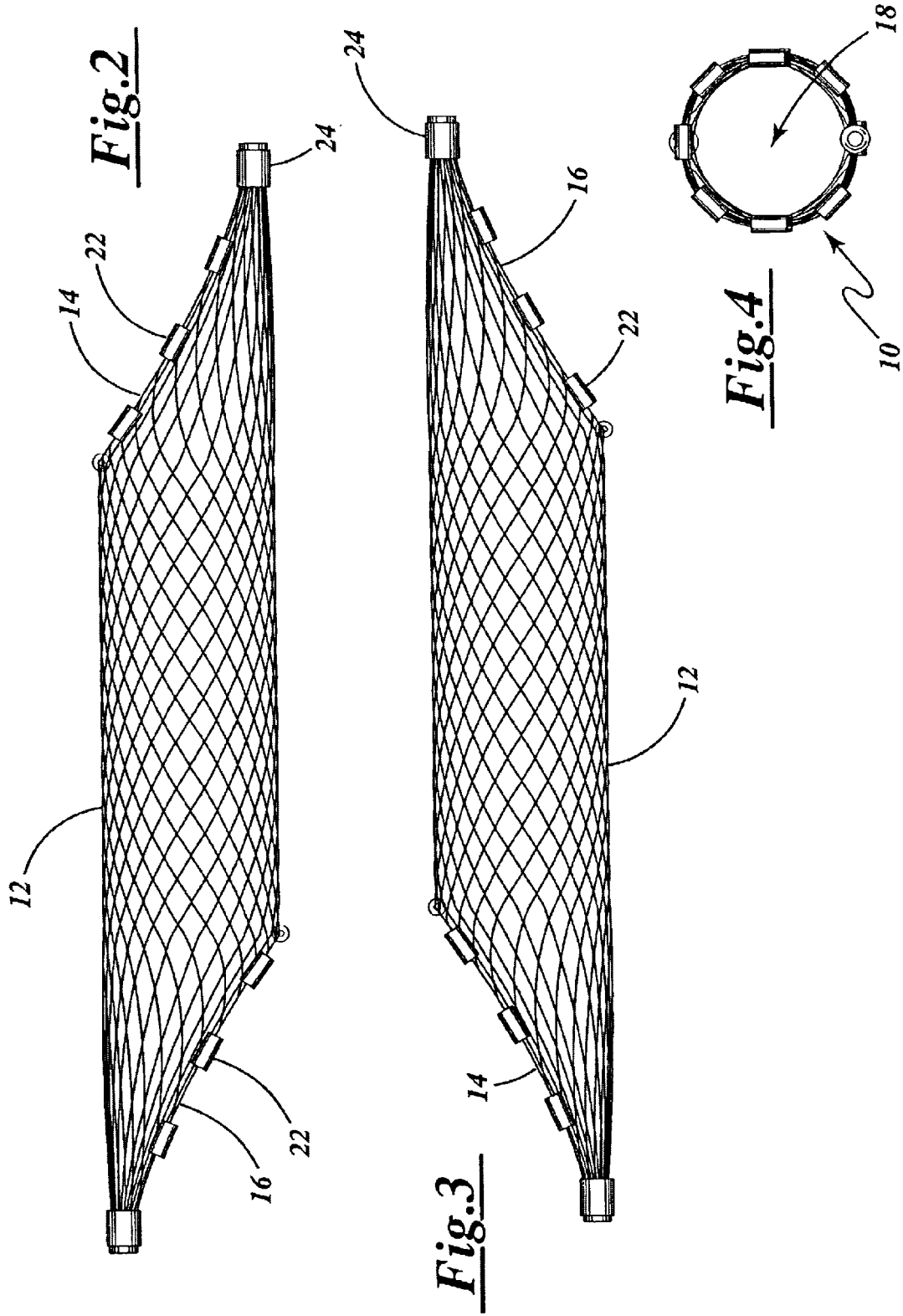

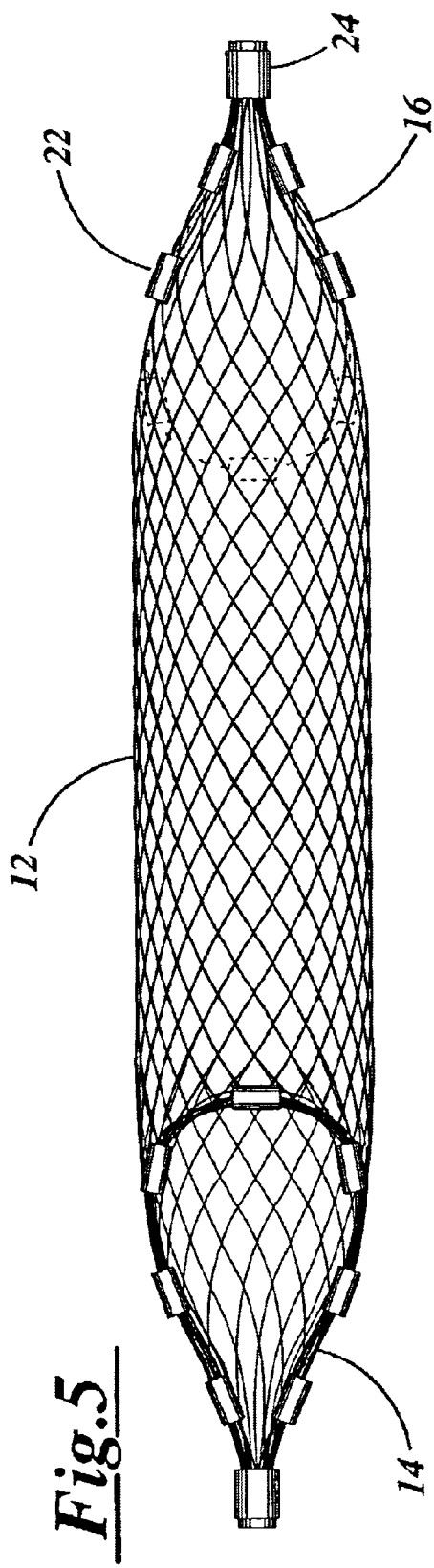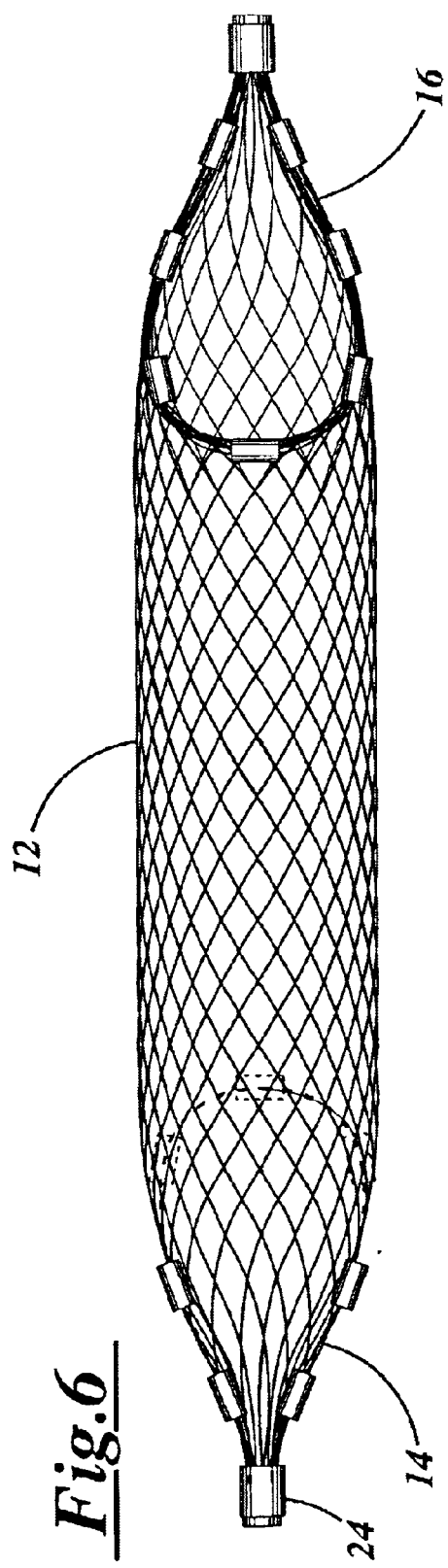

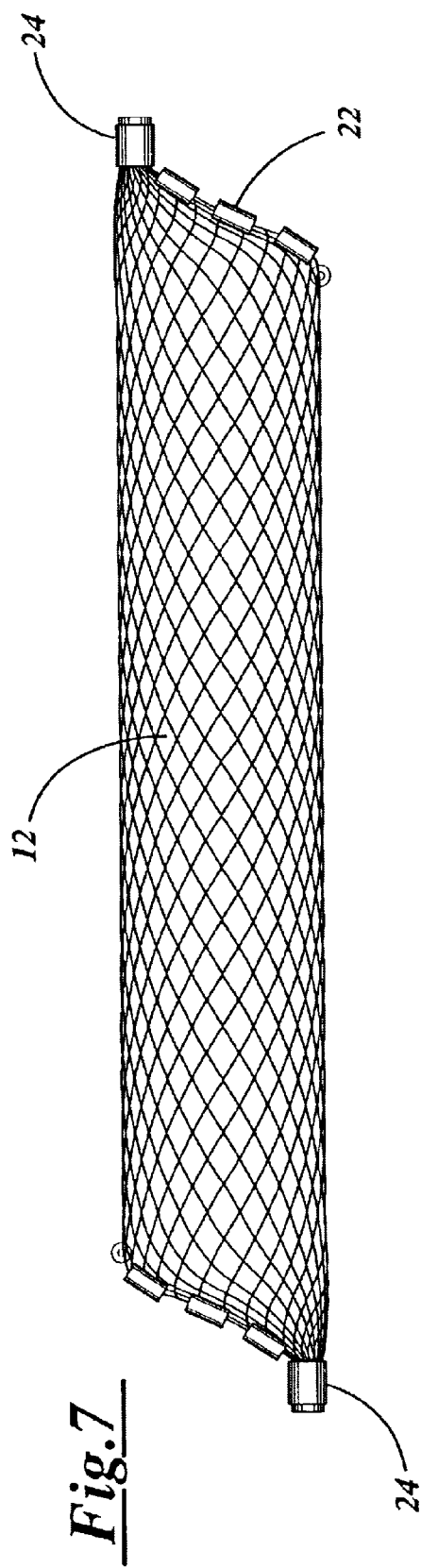
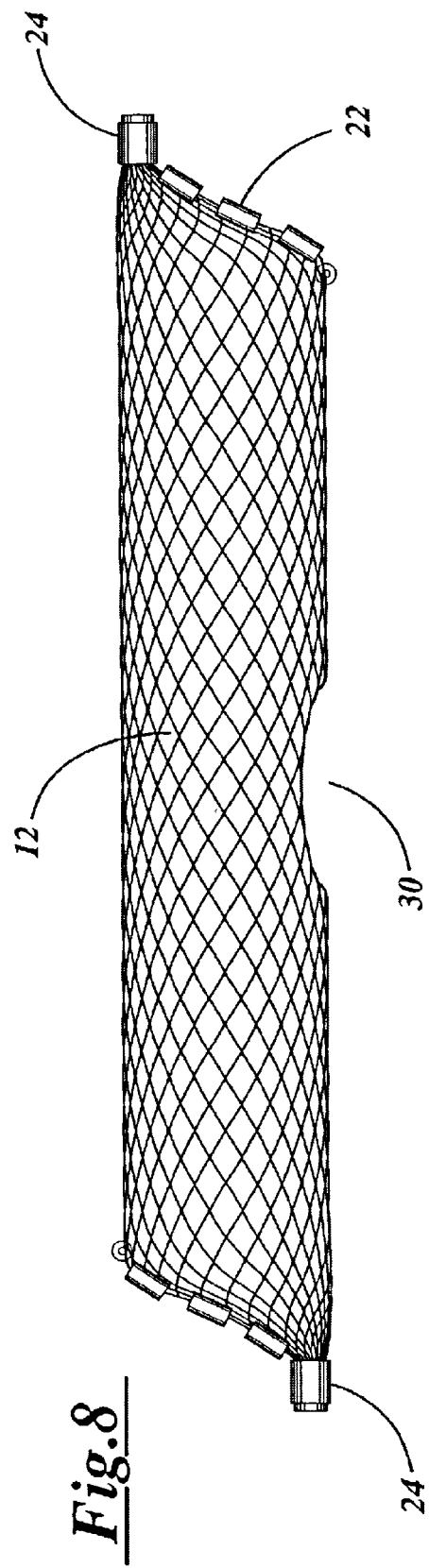

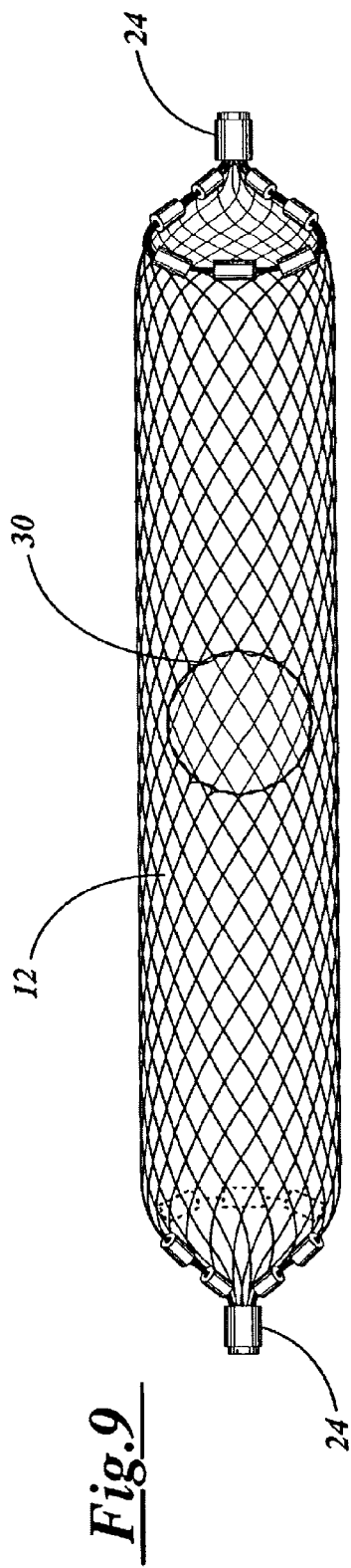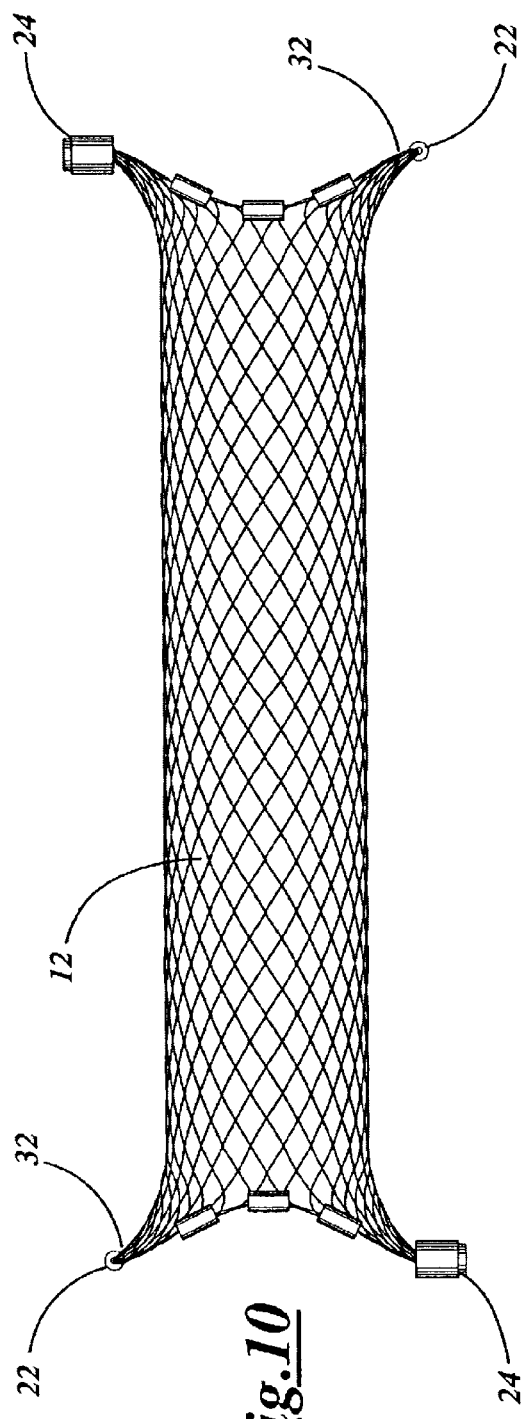

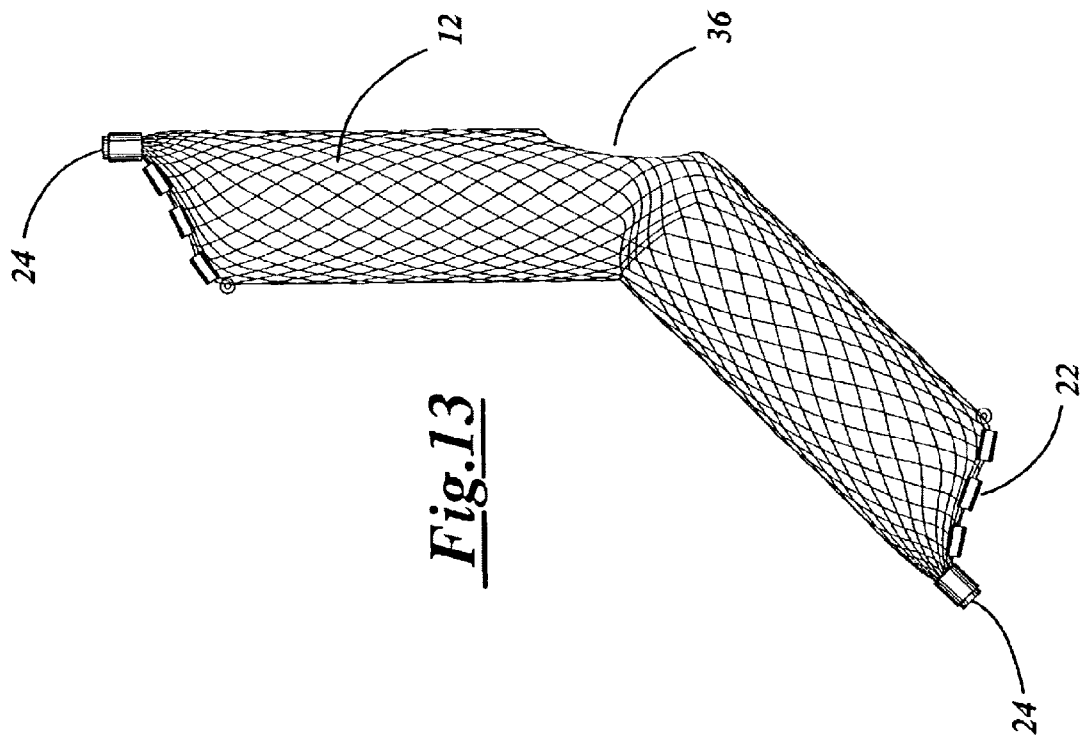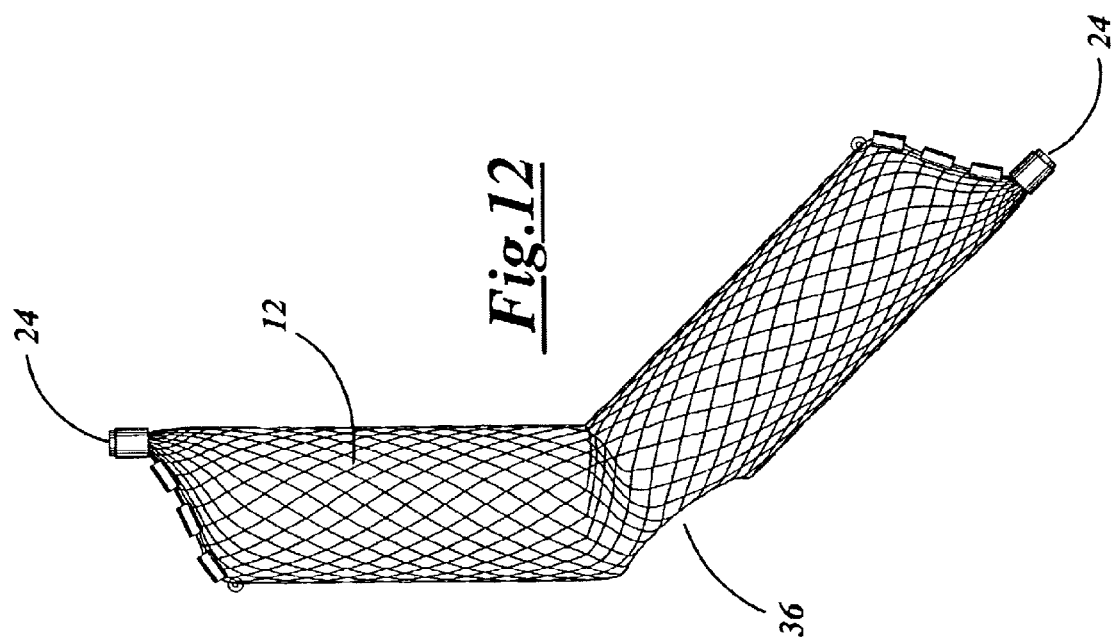

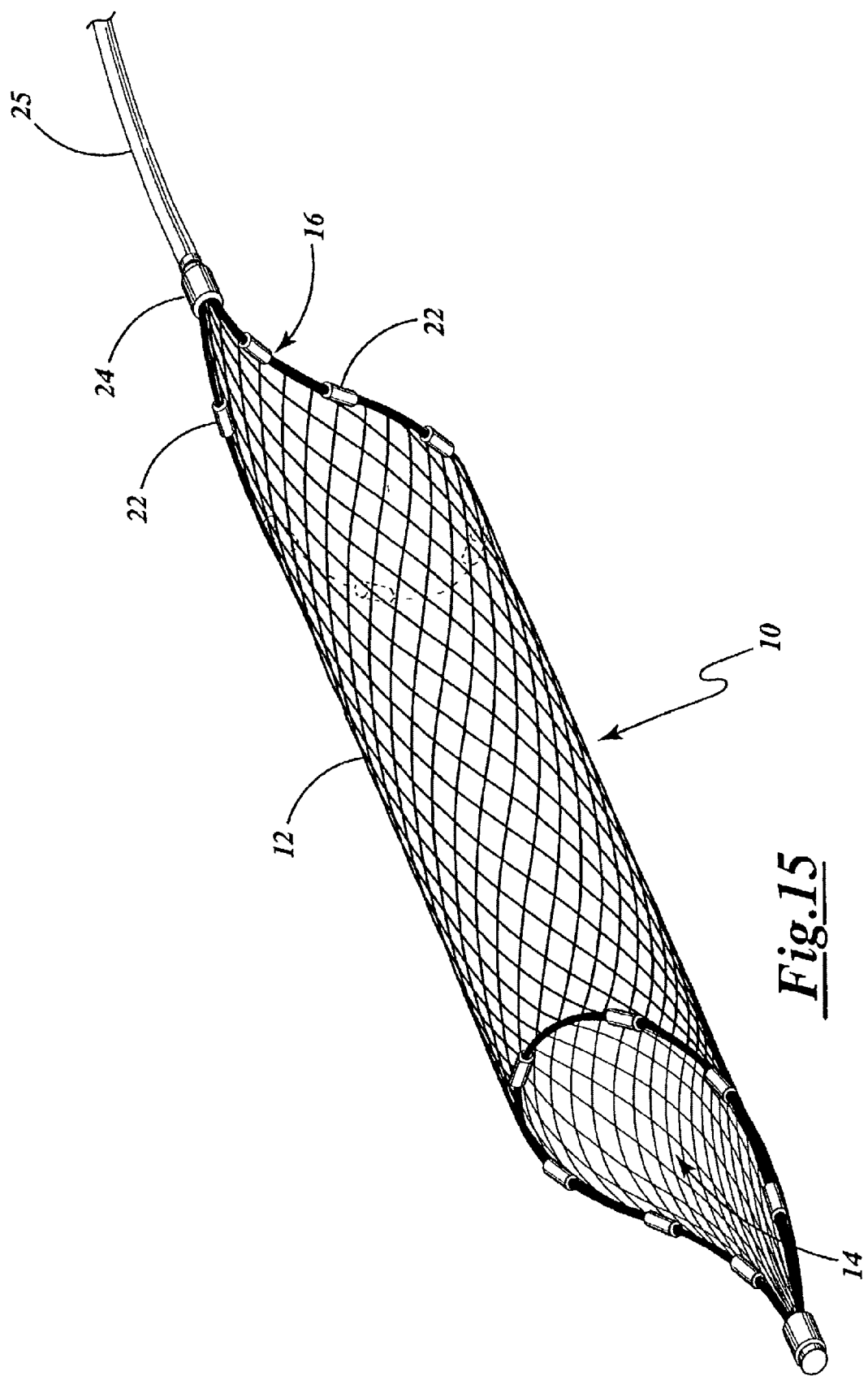

REPOSITIONABLE AND RECAPTURABLE VASCULAR STENT/GRAFT

CROSS-REFERENCE TO RELATED APPLICATION

This application is a divisional of application Ser. No. 09/535,600, filed Mar. 27, 2000, and now U.S. Pat. No. 6,468,301 entitled "REPOSITIONABLE AND RECAPTURABLE VASCULAR STENT/GRAFT".

I. FIELD OF THE INVENTION

The present invention relates generally to a device and minimally invasive procedure for treating a localized abnormal dilation of a lumen and more particularly, the present invention relates to a low profile stent suitable for use as a synthetic graft for the non-surgical treatment of an aneurysm, fistula, legion or the like in certain blood vessels and internal organs. The device made in accordance with the invention is retrievable and includes markers spaced about the ends of the device allowing an enhanced determination of the orientation of the device. The device is particularly well suited for delivery through a catheter or the like to a remote location in the patient's intravenous system or in analogous vessel or organ within the patient's body.

II. BACKGROUND OF THE INVENTION

A wide variety of stents and grafts have been used in various medical procedures. For example, stents and grafts (both biological and synthetic grafts) have been used to treat aneurysms and fistulas. Typically, the stent has a right circular cylindrical shape and is deliverable through a catheter to a specific location within a patient. The catheter may be used to reach a selected vessel within the vascular system wherein stenting of the vessel is desired. In U.S. Pat. No. 5,824,055 issued to Spiridigliozzi et al. a stent graft delivery system is described, wherein the graft is preferably constructed of a polyester fabric and may be held in position with a wide range of conventional stent designs. Although Spiridigliozzi et al. recognizes the need for a retrievable graft, they only describe a device that is retrievable and withdrawn when partially deployed. Hence, there is a need for a graft that is retrievable even after full deployment.

When a graft is delivered, it is also desirable to monitor the position of the graft after full deployment. Although markers capable of fluoroscopic detection have been attached to stents, the orientation of the ends of these stents remains difficult to determine when viewing the device in two dimensions. Lombardi et al. in U.S. Pat. No. 5,824,042 describes an endoluminal prostheses having position indicating markers on the prostheses, however, use of the markers to determine a rotational orientation of the ends is not described. Thus, there is a need for a stent having markers that indicate the rotational orientation of the stent, whether or not the device is viewed in two or three dimensions. The present invention addresses these and other needs that will become apparent to those skilled in the art from a review of the description of the present invention.

SUMMARY OF THE INVENTION

It is thus an object of the present invention to provide a retrievable, low-profile, self-expanding stent. The device of the present invention is preferably formed from a continuous tubular fabric, has a relaxed low-profile configuration, and includes clamps that allow for attachment of the device to an end of a delivery device or guide wire (allowing recovery of the device after deployment). In the preferred embodiment, the device is constructed from a metal fabric having a plurality of woven metal strands. The device has a proximal end and a distal end, and clamps or means for securing the metal fabric attached to each end. The clamps inhibit unraveling of the metal fabric. The configuration of the preferred embodiment has a substantially cylindrical relaxed configuration including a passageway between the two ends. Without any limitation intended, the specific shape of the device of the present invention is particularly well suited for treating an aneurysm of a vessel.

In one embodiment of the present invention, the device is constructed of a plurality of woven strands. The device has a proximal end and a distal end, each end having attached thereto a securing member that secures the woven strands together at each end, thereby inhibiting unraveling of the fabric. The device has a relaxed generally cylindrical configuration, wherein the relaxed cylindrical configuration includes a passageway extending through a central portion between each end of the device. The end portions of the device extend at an angle from the cylindrical main body portion of the device, wherein a plane of at least one end intersects a longitudinal axis of the cylindrical portion at an angle of at least one of acute and obtuse. The device further has a collapsed configuration for delivery through a catheter and channel in a patient's body.

Additionally, at least one end of the device includes markers spaced a predetermined distance around an outer perimeter edge of the end. Also, the securing member is attachable to a delivery device. The pitch and pick of the woven strands are such that the wire mesh is inherently thrombogenic, wherein a layer of fibrin forms on the surface of the device.

In another embodiment of the present invention, the ends of the device are flared, wherein a width of the ends is greater than a midsection of the device. In yet another embodiment of the invention, an aperture is formed in the midsection of the device, and is adapted for receiving an end of another device of the present invention. In still another embodiment of the present invention, the cylindrical main body is bent and includes an aperture formed in cylindrical main body proximate the bend. A first graft of this embodiment may be stretched and partially pulled through the aperture of a second graft of this embodiment. When the first graft is allowed to resume its relaxed configuration, the first and second grafts together form a "Y" shaped graft.

When forming these intravascular devices from a resilient fabric a plurality of resilient strands or wires are provided, with the fabric being formed by braiding the resilient strands to create a resilient material. The strands or wires have memory properties and are preferably made of a biocompatible metal alloy of known suitable construction. Either all or a portion of one or both of the outer and inner perimeter of the graft may be enclosed by a biocompatible material. Without any limitation intended, the biocompatible material may comprise a suitable known fabric manufactured by Gore, Inc. of Delaware.

In the preferred embodiment the braided fabric is deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric so treated defines a relaxed state of a medical device which can be stretched or expanded and deployed through a catheter into a channel in a patient's body. Those skilled in the art will appreciate that the cavities of the molds must mirror the desired shape of the device. Additionally, the mold includes cores and/or cams to adequately form the desired openings in each end of the device.

In use, a guide catheter is positioned and advanced in a patient's body such that the distal end of the catheter is adjacent a desired treatment site for treating a physiological condition. The medical device of the present invention having a predetermined shape is then stretched and inserted into the lumen of the catheter. The device is urged through the catheter and out the distal end, whereupon, due to its ability to retain a preset configuration, it will tend to substantially return to its relaxed state adjacent the treatment site. Once the device is fully deployed, the physician or user may confirm proper deployment through radiographs, fluoroscopy, or other known non-intrusive means of observing the position of the device within the patient. The guide wire or delivery catheter is then released from the clamp and removed.

BRIEF DESCRIPTION OF THE DRAWINGS

FIG. 2 is a back side elevational view of the vascular stent graft of the type shown in FIG. 1;

FIG. 3 is a front side elevational view of the vascular stent graft of the type shown in FIG. 1;

FIG. 4 is an end elevational view of the vascular stent graft of the type shown in FIG. 1;

FIG. 5 is a top plan view of the vascular stent graft of the type shown in FIG. 1;

FIG. 6 is a bottom plan view of the vascular stent graft of the type shown in FIG. 1;

FIG. 7 is a side elevational view of another embodiment of the present invention;

FIG. 8 is a side elevational view of yet another embodiment of the present invention;

FIG. 9 is a top plan view of the device of the type shown in FIG. 8;

FIG. 10 is a side elevational view of still another embodiment of the present invention;

FIG. 12 a front elevational view of another embodiment of the present invention;

FIG. 13 is a back elevational view of a device of the type shown in FIG. 12.

FIG. 15 shows a delivery device connected to a stent graft.

DETAILED DESCRIPTION OF THE PREFERRED EMBODIMENT

Figure 1:
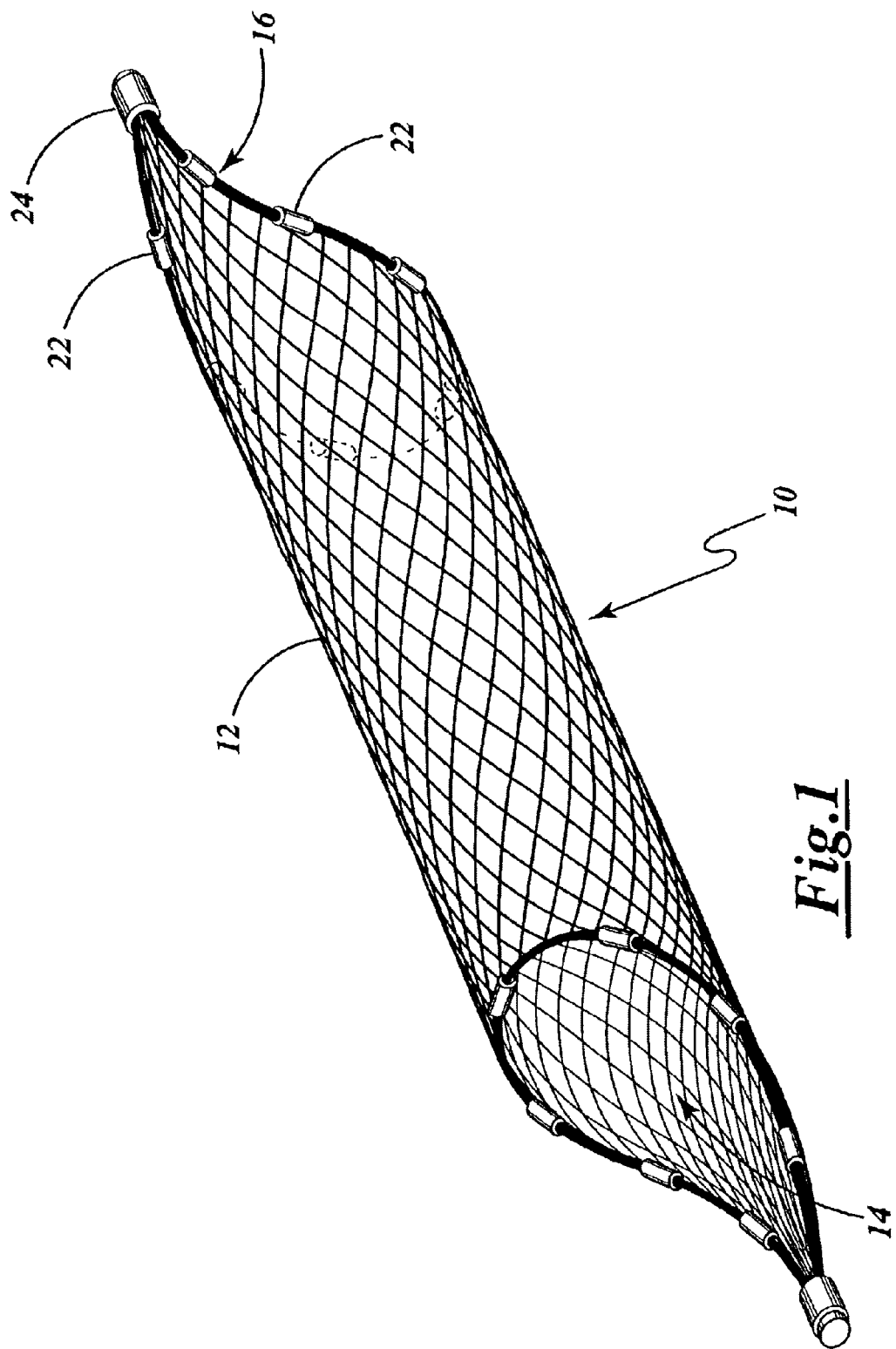
FIG. 1 is a perspective view of a retrievable self-expanding vascular stent graft of the present invention.

The following detailed description of the preferred embodiment in conjunction with the accompanying claims and drawings describes the invention in which like numerals in the several views refer to corresponding parts. The present invention represents broadly applicable improvements to self-expanding vascular stent graft devices. The embodiments detailed herein are intended to be taken as representative or exemplary of those in which the improvements of the invention may be incorporated and are not intended to be limiting.

The present invention provides a percutaneous catheter directed self-expanding retrievable stent graft 10 that is particularly well suited for treating an aneurysm. The stent graft 10 includes a tubular generally cylindrical main body portion 12 and angled end portions 14 and 16. The cylindrical portion 12 includes a passageway 18 extending between end portions 14 and 16. The stent graft 10 is preferably made from a tubular metal fabric including a plurality of woven metal strands. A clamp 24 is attached to each outer end of metal fabric, thereby inhibiting unraveling of the metal fabric. At least one of the clamps 24 is adapted for coupling to the end of a guidewire or catheter for delivery to a pre-selected site within the patient.

The tubular "fabric" is formed from a plurality of wire strands having a predetermined relative orientation between the strands. Those skilled in the art will appreciate that the pick and pitch of the braided wires may be varied depending upon the desired density of the fabric. The tubular fabric has metal strands which define two sets of essentially parallel generally spiraling and overlapping strands, with the strands of one set having a "hand", i.e. a direction of rotation, opposite that of the other set. This tubular fabric is known in the fabric industry as a tubular braid.

The pitch of the wire strands (i.e. the angle defined between the turns of the wire and the axis of the braid) and the pick of the fabric (i.e. the number of turns per unit length) as well as some other factors, such as the number of wires employed in a tubular braid, the size or diameter of each wire in the braid, and the diameter of the braid are all important in determining a number of important properties of the device. For example, the greater the pick and pitch of the fabric, and hence the greater the density of the wire strands in the fabric, the stiffer the device will be. Also, the greater the diameter of each wire of the braid, the stiffer the device will be. Having a greater wire density will also provide the device with a greater wire surface area, which will generally enhance the tendency that fibrin forms on the surface of the device. This thrombogenicity can be either enhanced by a coating of a thrombolytic agent, or abated by a coating of a lubricious, anti-thrombogenic compound. When using a tubular braid to form a device of the present invention, a tubular braid of about 4 mm in diameter having approximately 72 braided wires is suitable for fabricating a stent graft devices. Of course, those skilled in the art will appreciate that the number of braided wires may be increased substantially to more than 144 braided wires and the diameter may be increased or decreased depending upon the size of the vessel wherein the graft is to be positioned.

The wire strands of the tubular metal fabric are preferably manufactured from so-called shape memory alloys. A device may be manufactured from a shape memory alloy, wherein the shape of the device may be dependant on temperature or may be manufactured to be independent of temperature. When manufacturing a device from shape memory alloys to be independent of temperature changes, a preferred configuration can be fixed by heating the material above a certain phase change transition temperature to induce a change in the phase of the material. When the alloy is cooled back down, the alloy will "remember" the shape it was in during the heat treatment and will tend to assume that configuration independent of temperatures less than the heat treatment temperature, unless constrained from so doing.

Without any limitation intended, suitable wire strand materials may include a cobalt-based low thermal expansion alloy referred to in the field as ELGELOY, nickel-based high temperature high-strength "superalloys" (including nitinol) commercially available from, for example, Haynes International under the trade name HASTELLOY, nickel-based heat treatable alloys sold under the name INCOLOY by International Nickel, and a number of different grades of stainless steel. The important factor in choosing a suitable material for the wire strands is that the wires retain a suitable amount of the deformation induced by a molding surface (as described below) when subjected to a predetermined heat treatment.

In the preferred embodiment, the wire strands are made from a shape memory alloy, NiTi (known as nitinol) that is an approximately stoichiometric alloy of nickel and titanium and may also include other minor amounts of other metals to achieve desired properties. Handling requirements and variations of NiTi alloy composition are known in the art, and therefore such alloys need not be discussed in detail here. U.S. Pat. No. 5,067,489 (Lind) and U.S. Pat. No. 4,991,602 (Amplatz et al.), the teachings of which are incorporated herein by reference, discuss the use of shape memory NiTi alloys in guide wires. Such NiTi alloys are preferred, at least in part, because they are commercially available and more is known about handling such alloys than other known shape memory alloys. NiTi alloys are also very elastic and are said to be "super elastic" or "pseudo elastic". This elasticity allows a device of the invention to return to a preset configuration after deployment.

When forming a medical device in accordance with the present invention, an appropriately sized piece of tubular metal fabric is inserted into a mold, whereby the fabric deforms to generally conform to the shape of the cavities and cores within the mold. The shape of the cavities are such that the metal fabric deforms into substantially the shape of the desired medical device. Cores within the cavities are used to further form the shape of the fabric within the cavities. The ends of the wire strands of the tubular metal fabric should be secured to prevent the metal fabric from unraveling. A clamp 24, welding, or other suitable fastening device may be used to secure the ends of the wire strands. Further, it is to be understood that other suitable fastening means may be attached to the ends in other ways, such as by soldering, brazing, use of biocompatible cementious material or in any other suitable fashion.

During the molding procedure, a molding element may be positioned within the lumen of the tubular braid prior to insertion into the mold to thereby further define the molding surface. If the ends of the tubular metal fabric have already been fixed by a clamp or welding, the molding element may be inserted into the lumen by manually moving the wire strands of the fabric apart and inserting the molding element into the lumen of the tubular fabric. By using such a molding element, the dimensions and shape of the finished medical device can be fairly accurately controlled and ensures that the fabric conforms to the mold cavity.

The molding element may be formed of a material selected to allow the molding element to be destroyed or removed from the interior of the metal fabric. For example, the molding element may be formed of a brittle or friable material. Once the material has been heat treated in contact with the mold cavities and molding element, the molding element can be broken into smaller pieces which can be readily removed from within the metal fabric. If this material is glass, for example, the molding element and the metal fabric can be struck against a hard surface, causing the glass to shatter. The glass shards can then be removed from the enclosure of the metal fabric.

Alternatively, the molding element can be formed of a material that can be chemically dissolved, or otherwise broken down, by a chemical agent, which will not substantially adversely affect the properties of the metal wire strands. For example, the molding element can be formed of a temperature resistant plastic resin which is capable of being dissolved with a suitable organic solvent. In this instance, the metal fabric and the molding element can be subjected to a heat treatment to substantially set the shape of the fabric in conformance with the mold cavity and molding element, whereupon the molding element and the metal fabric can be immersed in the solvent. Once the molding element is substantially dissolved, the metal fabric can be removed from the solvent.

Care should be taken to ensure that the materials selected to form the molding element are capable of withstanding the heat treatment without losing its shape, at least until the shape of the fabric has been set. For example, the molding element could be formed of a material having a melting point above the temperature necessary to set the shape of the wire strands, but below the melting point of the metal forming the strands. The molding element and metal fabric could then be heat treated to set the shape of the metal fabric, whereupon the temperature would be increased to substantially completely melt the molding element, thereby removing the molding element from within the metal fabric.

Those skilled in the art will appreciate that the specific shape of the molding element produces a specific shape of the molded device. If a more complex shape is desired, the molding element and mold may have additional parts including a camming arrangement, but if a simpler shape is being formed, the mold may have few parts. The number of parts in a given mold and the shapes of those parts will be dictated almost entirely by the shape of the desired medical device to which the metal fabric will generally conform.

When the tubular braid, for example, is in its preformed relaxed configuration, the wire strands forming the tubular braid will have a first predetermined relative orientation with respect to one another. As the tubular braid is compressed along its axis, the fabric will tend to flare out away from the axis conforming to the shape of the mold. When the fabric is so deformed the relative orientation of the wire strands of the metal fabric will change. When the mold is assembled, the metal fabric will generally conform to the molding surface of the interior cavity. After undergoing the shape memory process, the resulting medical device has a preset relaxed configuration and a collapsed or stretched configuration which allows the device to be passed through a catheter or other similar delivery device. The relaxed configuration is generally defined by the shape of the fabric when it is deformed to generally to conform to the molding surface of the mold.

Once the tubular fabric is properly positioned within a preselected mold with the fabric generally conforming to the molding surface of the cavities therein, the fabric can be subjected to a heat treatment while it remains in contact with the molding surface. Suitable heat treatment processing of nitinol wire to set a desired shape are well known in the art. Spirally wound nitinol coils, for example, are used in a number of medical devices, such as in forming the coils commonly carried around distal links of guide wires. A wide body of knowledge exists for forming nitinol in such devices, so there is no need to go into great detail here on the parameters of a heat treatment for the nitinol fabric preferred for use in the present invention. Briefly, though, it has been found that holding a nitinol fabric at about 500 degrees centigrade to about 550 degrees centigrade for a period of about 1 to 30 minutes, depending upon the softness or hardness of the device to be made will tend to set the fabric in its deformed state, i.e., wherein it conforms to the molding surface of the mold cavities. At lower temperatures, the heat treatment time will tend to be greater (e.g., about 1 hour at about 350 degrees centigrade) and at higher temperatures the time will tend to be shorter (e.g., about 30 seconds at about 900 degrees centigrade). These parameters can be varied as necessary to accommodate variations in the exact composition of the nitinol, prior heat treatment of the nitinol, the desired properties of the nitinol in the finished article, and other factors known to those skilled in this field.

Instead of relying on convection heating or the like, it is also known in the art to apply an electrical current to the nitinol to heat it. In the present invention, this can be accomplished by, for example, connecting electrodes to each end of the metal fabric. The wire can then be heated by resistance heating of the wires in order to achieve the desired heat treatment, which will tend to eliminate the need to heat the entire mold to the desired heat treating temperature in order to heat the metal fabric to the desired temperature. The materials, molding elements and methods of molding a medical device from a tubular or planar metal fabric are further described in U.S. Pat. No. 5,725,552.

Heat treating the metal fabric at temperatures ranging between 500–550 degrees centigrade substantially sets the shapes of the wire strands in a reoriented relative position conforming the shape of the fabric to the molding surface. When the metal fabric is removed from the mold, the fabric maintains the shape of the molding surfaces of the mold cavities to thereby define a medical device having a desired shape. After the heat treatment, the fabric is removed from contact with the molding cavity and will substantially retain its shape in a deformed state. If a molding element is used, this molding element can be removed as described above.

The time required for the heat treating process will depend in large part upon the material of which the wire strands of the metal fabric are formed and mass of the mold, but the time and temperature of the heat treatment should be selected to substantially set the fabric in its deformed state, i.e., wherein the wire strands are in their reoriented relative configuration and the fabric generally conforms to the molding surface. The required time and temperature of the heat treatment can vary greatly depending upon the material used in forming the wire strands. As noted above, one preferred class of materials for forming the wire strands are shape memory alloys, with nitinol, a nickel titanium alloy, being particularly preferred. If nitinol is used in making the wire strands of the fabric, the wire strands will tend to be very elastic when the metal is in its austenitic phase; this very elastic phase is frequently referred to as a super elastic or pseudo elastic phase. By heating the nitinol above a certain phase transition temperature, the crystal structure of the nitinol metal will tend to "set" the shape of the fabric and the relative configuration of the wire strands in the positions in which they are held during the heat treatment.

Once a device having a preselected shape has been formed, the device may be used to treat a physiological condition of a patient. A medical device suitable for treating the condition is selected. Once the appropriate medical device is selected, a catheter or other suitable delivery device may be positioned within a channel in a patient's body to place the distal end of the delivery device adjacent the desired treatment cite. The delivery device (not shown) can take any suitable shape, but desirably comprises an elongate flexible shaft having a threaded distal end. The delivery device can be used to urge the medical device through the lumen of a catheter for deployment in a patient's body. When the device is deployed out the distal end of the catheter, the device will still be retained by the delivery device. Once the medical device is properly positioned within the patient the metal shaft or guidewire can be rotated about its axis to unscrew the medical device from the threaded distal end of the shaft. The catheter and guidewire are then withdrawn.

By keeping the medical device attached to the delivery means, the operator can retract the device for repositioning, even after full deployment from the catheter, if it is determined that the device is not properly positioned. A threaded clamp attached to the medical device allows the operator to control the manner in which the medical device is deployed out the distal end of the catheter. When the device exits the catheter, it will tend to resiliently return to a preferred relaxed shape. When the device springs back into this shape, it may tend to act against the distal end of the catheter effectively urging itself forward beyond the end of the catheter. Since the threaded clamp can enable the operator to maintain a hold on the device during deployment, the spring action of the device can be controlled by the operator to ensure proper positioning during deployment.

The medical device can be stretched into its collapsed configuration and inserted into the lumen of the catheter. The collapsed configuration of the device may be of any shape suitable for easy passage through the lumen of a catheter and proper deployment out the distal end of the catheter. For example, the device may have a relatively elongated collapsed configuration wherein the device is stretched along its longitudinal axis. This collapsed configuration can be achieved simply by stretching the device generally along its axis, e.g. by manually grasping the clamps and pulling them apart, which will tend to collapse the relaxed generally cylindrical portion of the device inwardly toward the device's axis. Loading such a device into a catheter may be done at the time of implantation and does not require pre-loading of the introducer or catheter.

When the device is deployed in a patient, thrombi will tend to collect on the surface of the wires. By having a greater wire density, the total surface area of the wires will be increased, increasing the thrombotic activity around the perimeter of the device. It is believed that forming the stent graft from a 4 mm diameter tubular braid having a pick of at least about 40 and a pitch of at least about 30 will provide sufficient surface area to efficiently create a desired lumen within the vessel. If it is desired to increase the rate at which the perimeter of the device occludes, any of a wide variety of known thrombotic agents can be applied to the device. Those skilled in the art will appreciate that an occluding membrane, fiber, or mesh may be partially or completely wrapped around or within the device to further create a desired lumen.

The Figures illustrate the preferred embodiment of the stent graft 10 wherein a passageway extends through a central portion of the device. The stent graft device 10 of the preferred embodiment includes a tubular generally cylindrical main body portion 12 and angled end portions 14 and 16. The cylindrical portion 12 includes a passageway 18 extending between end portions 14 and 16 (see FIGS. 1 and 4). Without any limitation intended, during the formation of the device 10, the end of each woven strand is attached to a clamp 24. The ends of the woven strands deform about the perimeter to create an open end and angle towards the clamp 24. Markers 22 are attached to the perimeter of one or both open ends 14 and 16 and the shape of the ends in combination with the position of the markers 22 allow for an accurate determination of the orientation of the ends 14 and 16. Those skilled in the art will appreciate that the device of the preferred embodiment is well suited for the non-surgical treatment of an aneurysm, fistula, legion or the like in certain blood vessels and internal organs.

The clamps 24 tying together the wire strands at corresponding ends serve to connect the device 10 to a delivery system. In the embodiment shown in FIG. 15, at least one of the clamps 24 is generally cylindrical in shape and has a threaded bore suitable for receiving a threaded end of a guidewire 25. The clamps 24 receive the ends of the woven strands of the metal fabric to substantially prevent the wires from moving relative to one another. Those skilled in the art will appreciate that the device 10 is sized in proportion to the aneurysm to be treated.

Referring next to FIG. 7 an alternate preferred embodiment of the present invention is shown. The end portions of the device extend at an angle from the cylindrical main body portion 12 of the device, wherein a plane of at least one end intersects a longitudinal axis of the cylindrical portion at an angle of at least one of acute and obtuse, but wherein the angle is not as drastic as shown in FIG. 1.

Figure 11:
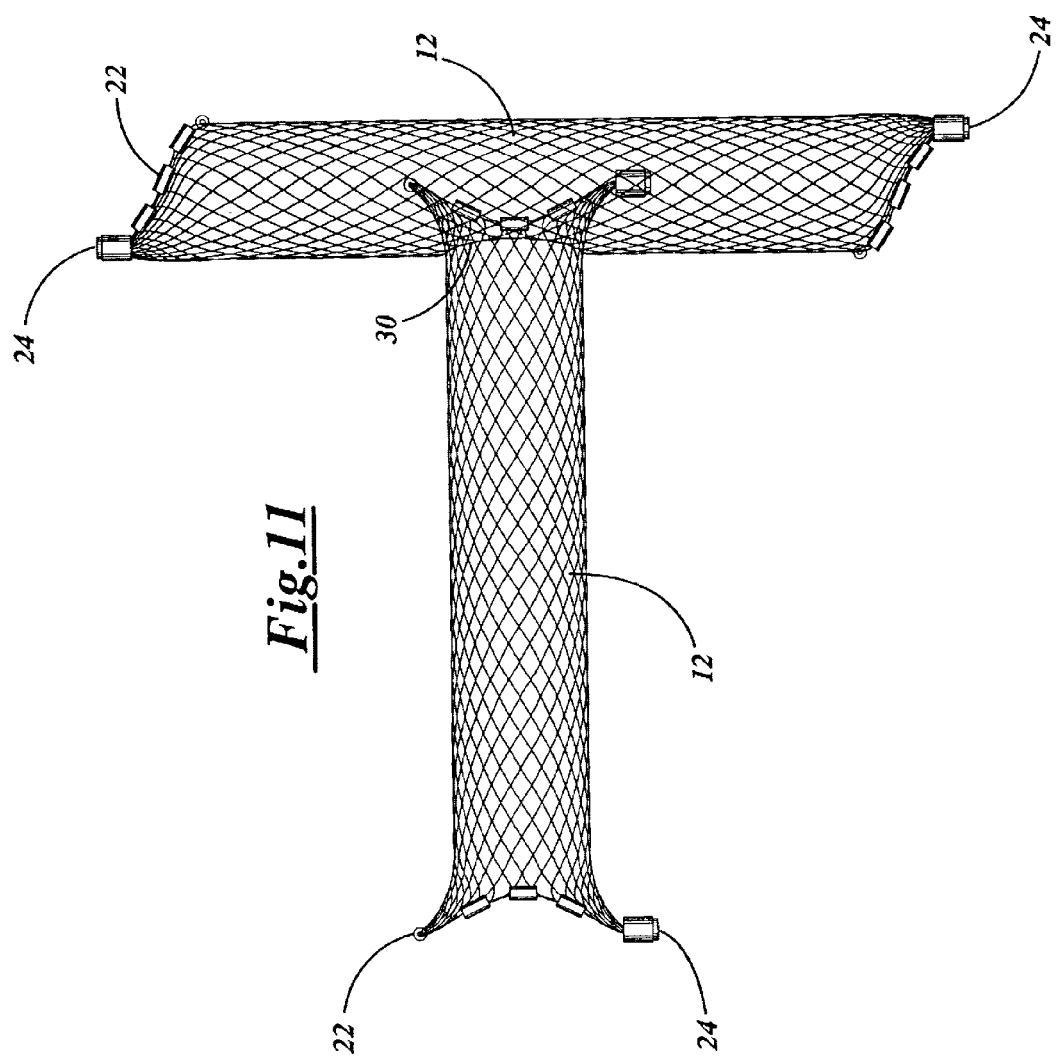
FIG. 11 shows the device of the type shown in FIG. 10 extending from an aperture of the device of the type shown in FIGS. 8 and 9.

FIGS. 8 and 9 show another embodiment of the invention, wherein an aperture 30 is formed in the midsection of the device. FIG. 10 shows another embodiment of the invention wherein the ends are flared outward to create a greater width of the device at the ends. FIG. 11 shows the device of the type shown in FIG. 10 extending through the aperture 30 of the device of the type shown in FIGS. 8 and 9. The flared end 32 inhibits the device from migrating out of the aperture 30. Those skilled in the art that a combination of the embodiments of the present invention as shown in FIG. 11 is particularly well suited for grafting or stenting, for example, the pulmonary branch. Alternatively, the flared device shown in FIG. 10 could be used to shunt, for example, a PDA.

Figure 14:
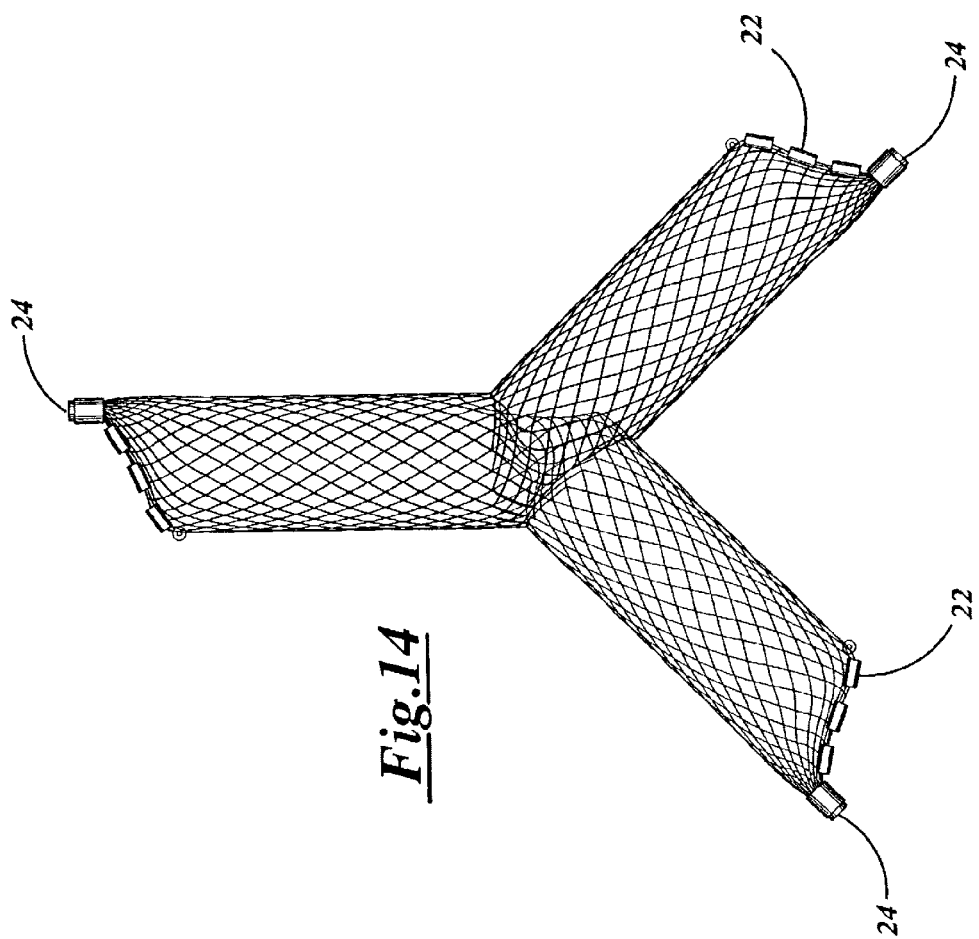
FIG. 14 is a front elevational view of a first device of the type shown in FIG. 12 partially extending from a second device of the type shown in FIG. 12.

In still another embodiment of the present invention shown in FIGS. 12–14, the cylindrical main body 12 is bent and includes an aperture 36 formed in cylindrical main body 12 proximate the bend. The cylindrical main body has a first portion having a larger diameter which is sized to fit within, for example, the abdominal aorta and a second portion having a smaller diameter sized to fit within, for example, the iliac artery. Without limitation, in the preferred embodiment the length of the first portion exceeds the length of the second portion. FIG. 14 shows a first graft identified as numeral 40 stretched and partially pulled through the aperture 36 of a second graft identified as numeral 42. When the first graft 40 is allowed to resume its relaxed configuration, the first and second grafts 40 and 42 together form a "Y" shaped graft. In use, the second graft 42 is delivered by known techniques to the desired portion in the "Y" branch of a vessel. A second delivery device then extends into an end of the second branch and out the aperture 36. The first graft 40 is then partially released and simultaneously the delivery device is withdrawn until a portion of the first graft 40 is positioned within the second graft 42 as shown in FIG. 14. The "Y" shaped graft may be used to non-surgically treat an aneurysm, fistula, legion or the like in a "Y" shaped juncture of certain blood vessels. For example, those skilled in the art will appreciate that the "Y" shaped graft may be particularly useful as a triple A (AAA) graft for the repair of an abdominal aortic aneurysm.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A collapsible medical device, comprising a fabric including a plurality of woven strands, said medical device having a proximal end and a distal end, each end having permanently attached thereto a clamp for securing the woven strands, thereby inhibiting unraveling of the fabric, said at least one of the clamps including a means for releasable attachment thereof to a delivery device, said medical device having a relaxed configuration, wherein said relaxed configuration includes a passageway extending through a central portion between each end, and further including an aperture formed in a side portion of the relaxed configuration, said medical device further having a collapsed configuration for delivery through a channel in a patient's body.

2. The device according to claim 1, wherein both ends include markers spaced a predetermined distance around an edge of each of said ends.

3. The device according to claim 1, wherein said medical device is formed from a metal fabric consisting of a plurality of woven metal strands.

4. The device according to claim 1, wherein said clamps are aligned on an outer edge of each of said ends.

5. The device as recited in claim 1, wherein said relaxed configuration is in a bent shape.

6. A collapsible medical device, comprising a fabric including a plurality of woven strands, said medical device having a proximal end and a distal end, each end having permanently attached thereto a clamp member for inhibiting unraveling of the fabric, at least one of the clamp members having means for releasable attachment to a delivery device, said medical device having a relaxed configuration, wherein said relaxed configuration includes a passageway extending through a central portion between each end, and further wherein at least one end of said relaxed configuration has a width greater than the width of a central portion of the relaxed configuration, said medical device further having a collapsed configuration for delivery through a channel in a patient's body.

7. The device according to claim 6, wherein at least one end includes markers spaced a predetermined distance around an edge of said at least one end.

8. The device according to claim 6, wherein both ends include markers spaced a predetermined distance around an edge of each of said ends.

9. The device according to claim 6, wherein said medical device is formed from a metal fabric consisting of a plurality of woven metal strands.

10. The device according to claim 6, wherein said clamp members are aligned on an outer edge of each of said ends.

* * * * *

UNITED STATES PATENT AND TRADEMARK OFFICE
CERTIFICATE OF CORRECTION

PATENT NO.     : 6,932,837 B2
DATED          : August 23, 2005
INVENTOR(S)    : Kurt Amplatz and Michael Afremov It is certified that error appears in the above-identified patent and that said Letters Patent is hereby corrected as shown below:

Column 10,
Line 26, after "a patient's body" insert -- , and wherein at least one end includes markers spaced a predetermined distance around an edge of said at least one end --.
Line 47, before "central" replace "a" with -- the --.

Signed and Sealed this

Eighth Day of November, 2005

JON W. DUDAS
*Director of the United States Patent and Trademark Office*